US006602290B2

United States Patent
Esnouf et al.

(10) Patent No.: US 6,602,290 B2
(45) Date of Patent: *Aug. 5, 2003

(54) SURGICAL AID FOR CONNECTIVE TISSUE GRAFTING AND METHOD FOR EMPLOYING SAME

(75) Inventors: Philip Stuart Esnouf, Toorak (AU); Bruce Richard Tylden Love, Kew (AU)

(73) Assignee: Centerpulse Orthopedics Inc., Austin, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 85 days.

(21) Appl. No.: 09/380,210

(22) PCT Filed: Feb. 25, 1998

(86) PCT No.: PCT/AU98/00120

§ 371 (c)(1),
(2), (4) Date: Nov. 19, 1999

(87) PCT Pub. No.: WO98/37835

PCT Pub. Date: Sep. 3, 1998

(65) Prior Publication Data

US 2002/0055749 A1 May 9, 2002

(30) Foreign Application Priority Data

Feb. 25, 1997 (AU) .............................. PO 5309

(51) Int. Cl.[7] .................................. A61F 2/08
(52) U.S. Cl. .............. 623/13.16; 623/908; 623/13.15
(58) Field of Search ................. 623/13.11, 13.15, 623/13.16, 13.18, 908; 606/148

(56) References Cited

U.S. PATENT DOCUMENTS

| 3,971,670 A | | 7/1976 | Homsy |
| 4,455,690 A | * | 6/1984 | Homsy .................... 623/13.15 |
| 4,467,478 A | | 8/1984 | Jurgutis ............................ 3/1 |
| 4,743,252 A | | 5/1988 | Martin, Jr. et al. ............. 623/1 |
| 4,883,486 A | * | 11/1989 | Kapadia et al. .......... 623/13.15 |
| 4,942,875 A | | 7/1990 | Hlavacek et al. .......... 606/230 |
| 4,987,665 A | | 1/1991 | Dumican et al. ............. 28/218 |
| 5,425,766 A | * | 6/1995 | Bowald .................... 623/13.18 |
| 5,456,721 A | | 10/1995 | Legrand ...................... 623/13 |

FOREIGN PATENT DOCUMENTS

| EP | 0 328 401 A1 | 8/1989 |
| EP | 0 459 914 A1 | 4/1991 |
| FR | 2669527 | 7/1991 |
| FR | 2724839 | 9/1994 |
| GB | 2181653 | 4/1987 |
| WO | 9603084 | 2/1996 |
| WO | 9603086 | 2/1996 |
| WO | 9733535 | 9/1997 |

* cited by examiner

Primary Examiner—Corrine McDermott
Assistant Examiner—Brian E Pellegrino
(74) Attorney, Agent, or Firm—Kenneth S. Barrow

(57) ABSTRACT

A device for use in ligament grafting includes a holder for receiving a ligament graft. A sheath is mounted over the holder in an expanded diameter state. The ligament graft is removed from the hollow body with the sheath so that the ligament graft is captured in the sheath in a reduced diameter state and a substantial length of the sheath extends from opposite ends of the graft.

17 Claims, 7 Drawing Sheets

SURGICAL AID FOR CONNECTIVE TISSUE GRAFTING AND METHOD FOR EMPLOYING SAME

BACKGROUND

This invention relates to a surgical aid and a method for employing same. The surgical aid of the invention is particularly useful in connective tissue grafting procedures, such as ligament grafting as may be utilised in the surgical reconstruction of a joint.

Connective tissue surgery can involve certain difficulties which are not experienced in other surgical procedures, in view of the significant tension which is often required to be endured by the connective tissue after surgery. For example, in the surgical reconstruction of the anterior cruciate ligament of a human knee, often a tissue graft is taken from healthy connective tissue and affixed in place of the damaged ligament. Because of the relatively high tensive load bearing requirements of the connective tissues in the knee joint, it is vitally important that the ends of the tissue graft attach securely at the bone insertion points. It is therefore desirable to enhance the fixation of the graft at each end thereof.

Depending upon the particular surgical procedure employed, a connective tissue graft may be required to be passed through bores which have been drilled in bone structures. The drilled bores are preferably as close in diameter as possible to the size of the end portions of the graft where the graft ends are to be attached therein. Thus, sometimes considerable force may be required in order to draw the tissue graft through the hole in order to overcome the frictional forces acting between the graft and aperture surface. In previous surgical techniques it has been known to attach a suture to the end of the tissue graft for the purpose of drawing the graft through the aperture, but the suture can sometimes tear the graft tissue if pulled too hard. In the worst case the tissue graft may be ruined, with the result of serious consequences for the graft recipient. Further tension may be required to be applied to the graft during the surgical procedure in some instances where it is desirable for the graft to be under tension when surgically attached.

Another technique has been proposed in U.S. Pat. No. 5,456,721 (Legrand). In that proposal, a tendon is located within a resorbable yarn. In a first embodiment the ends of the sheath are formed with loops which are engaged by a U-shaped member which is used to interconnect the loops with the graft and bone tissue. In another technique, the sheath is located within an insertion tube, the head of which forms an anchoring device for one end of the graft. The present invention utilises a bioabsorbable sheath but the sheath has different properties so that it can be used in novel and advantageous ways.

SUMMARY

The object of the present invention is to provide a novel sheath for use in ligament grafting, the sheath having elongate pliable ends to facilitate insertion and positioning of the graft.

Another object of the present invention is to provide a novel device for assisting in ligament grafting.

Another object of the present invention is to provide a method of facilitating placement of a ligament graft utilising a sheath having elongate end portions which can be pulled to facilitate placement and positioning of the graft.

A further object of the invention is to provide a novel ligament graft assembly which includes a sheath having elongate end portions which facilitate insertion and placement of the graft.

According to the present invention there is provided a sheath for use in ligament grafting, said sheath being formed from or including bioabsorbable material and having a relaxed state in which the sheath has a diameter in the range about 8 mm to about 15 mm and a stretched state in which the length of the sheath is at least five times its length in its relaxed state.

Preferably the length of the sheath in the stretched state is about ten times the length in its relaxed state.

Preferably the diameter of the sheath in its stretched state is about 0.1 to 0.25 of the diameter in the relaxed state.

Preferably the diameter of the sheath in its relaxed state is in the range 1.5 to 2.5 mm.

The invention also provides a device for assisting in ligament grafting comprising:
  a holder having a hollow body which is open at both ends for receiving, in use, a ligament graft;
  a sheath mounted over the hollow body;
  said sheath being formed from or including bioabsorbable material and having an expanded diameter state in which engages the hollow body and a reduced diameter state in which its length is substantially greater than its length in the expanded diameter state, the arrangement being such that, in use, a ligament graft can be located within the hollow body and a one end of the sheath pulled from one end of the hollow body so that a first end of the graft is withdrawn from the body and retained in the sheath so the body can then be removed from the other end of the sheath whereby a ligament graft assembly is formed in which the graft is located in an intermediate portion of the sheath in its reduced diameter state.

The invention also provides a method of facilitating placement of a ligament graft comprising the steps of forming a ligament graft assembly by placing a ligament graft within a sheath whilst the sheath is in an expanded diameter state and pulling respective ends of the sheath away from the graft so that the graft remains enveloped by an intermediate portion of the sheath, the end portions of the sheath being elongate and in a reduced diameter state, forming first and second holes in first and second bones, pulling one of said end portions through said holes so that the graft is carried with the sleeve until one end of the graft is located in the first hole and the other end of the graft is located in the second hole.

The invention also provides a ligament graft assembly comprising a ligament graft and a sleeve formed from bioabsorbable material, the graft being located within an intermediate portion of the sleeve and end portions of the sleeve being elongate and cord like to enable placement ends of the graft at a respective graft site by pulling one or both of said end portions of the sheath.

Preferably, the sheath is formed from strands of bioabsorbable material having a thickness in the range 0.06 to 0.55 mm and preferably about 0.175 mm.

Preferably further, the material is formed as an open mesh fabric, the mesh size of which is 2.5 to 3.5 mm (as measured when the sheath is flat and relaxed).

Preferably further, the sheath has substantial linear expansion, preferably in the range from 10 to 20 times. For instance, if a length of the sheath material in a relaxed state is say 30 mm in length (and having a diameter of the order of say 20 mm), it can be stretched to form a string or cord like structure having a length say of about 300 mm. This enables the graft to be located in a central part of the sheath which is partly expanded and the end parts of the sheath to serve as strings or cords for use in insertion and placement of the graft.

The invention also provides a sheath for a connective tissue graft comprising a mesh of bioabsorbable strands in the form of a tube which is collapsable about its axis to ensheath a connective tissue graft inserted therein to allow axial tension applied to the sheath to be at least partially transmitted to the graft.

The sheath is preferably braided from a plurality of strands of thread or yarn. Alternatively, the sheath may be woven or knitted to form the tube structure, also preferably from a plurality of strands. The weave or knit pattern is preferably locked so that the sheath does not lose its integrity by running or the like if some of the strands are broken.

The strands forming the sheath may all be constructed from a bioabsorbable material, although it is also possible for only a proportion of the strands to be bioabsorbable and the remaining strands constructed from non-absorbable biocompatible materials. Some suitable bioabsorbable materials include polyglycolic acid (PGA) and polylactic acid (PLA) materials formed into fibres. Poliglecaprone and polydioxanone materials can also be utilised.

In one particular form of the invention, the sheath is formed from 24 strands of suture material, each 4/O polyglycolic acid, interwoven into a tubular structure having a relaxed circumference of about 2 centimeters.

The mesh sheath of preferred embodiments of the invention may additionally provide a framework for the impregnation of growth enhancing factors, cultured cells or other pharmacological agents, to aid in improved recovery from the graft surgery.

In use of the sheath for connective tissue graft surgery, the graft would typically be inserted into a section of the sheath material which is of a length so as to be somewhat longer than the graft itself. The ends of the sheath may then be pulled to apply tension to the sheath to facilitate the desired collapsing contraction of the sheath about the outside of the graft.

With the graft ensheathed by the mesh, a component of axial tension applied to the sheath is transmitted to the graft itself. The graft may then be attached into its site of application with the sheath in place, and end portions of the sheath material trimmed away. Preferably the fixing means applied to the graft also fixes the sheath in place. For example where interference screws are used for attachment of the graft ends, the screws may be inserted through the sheath mesh, which can aid in fixation of the graft in the short term at least.

In accordance with another aspect of the invention, there is provided a method of connective tissue grafting comprising inserting a tissue graft into a length of sheath constructed as described broadly above, applying axial tension to the sheath so as to contract the sheath about the graft, utilising the sheath to position the graft into its site of application, and affixing the graft and sheath into position.

In order to facilitate insertion of the graft into the tube of sheath material, a tubular mesh holder may be provided having a diameter sufficient to allow the graft to pass therethrough. The mesh holder is inserted into one end of the sheath tube and then the graft is passed through the mesh holder and into the sheath.

The sheath of embodiments of the invention allows delivery of a graft held therein to its site of application without attaching sutures or the like to the graft itself, which therefore avoids potential damage to the graft during insertion. The sheath additionally provides a measure of protection to the graft by surrounding the graft during the insertion procedure. If desired, the graft may be maintained under tension during the insertion and attachment procedure by maintaining tension on the ends of the sheath. The sheath is fixed in place together with the graft, and is absorbed, or at least partially absorbed, over a period of time following insertion into the body.

The invention is described in greater detail hereinafter, by way of example only, with reference to the accompanying drawings, wherein:

BRIEF DESCRIPTION OF THE DRAWING FIGURES

Figure 5:
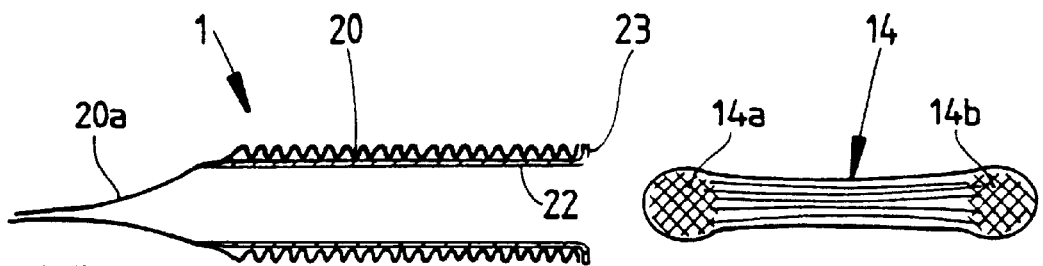
Figure 6:
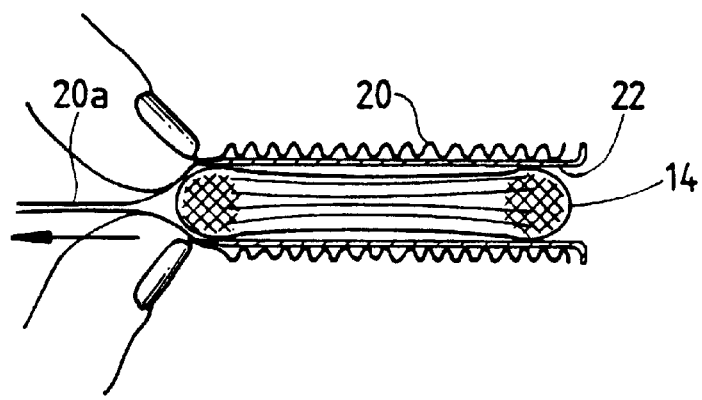
Figure 7:
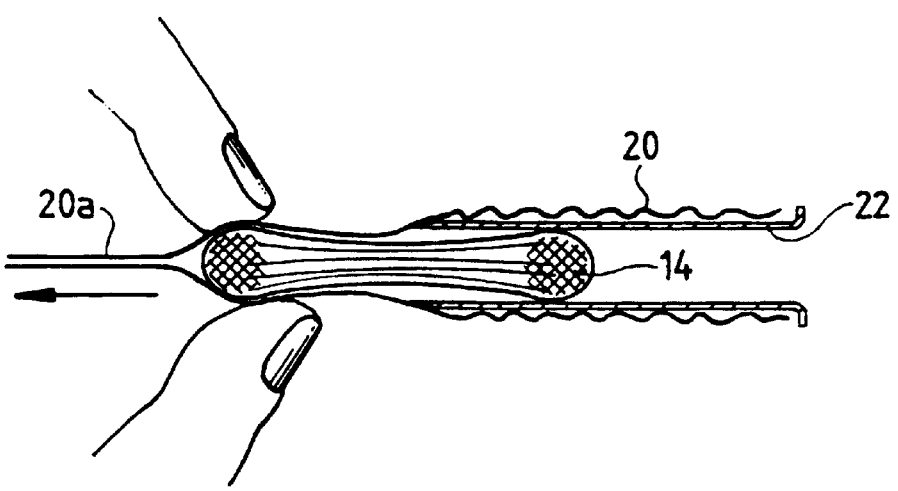
Figure 8:
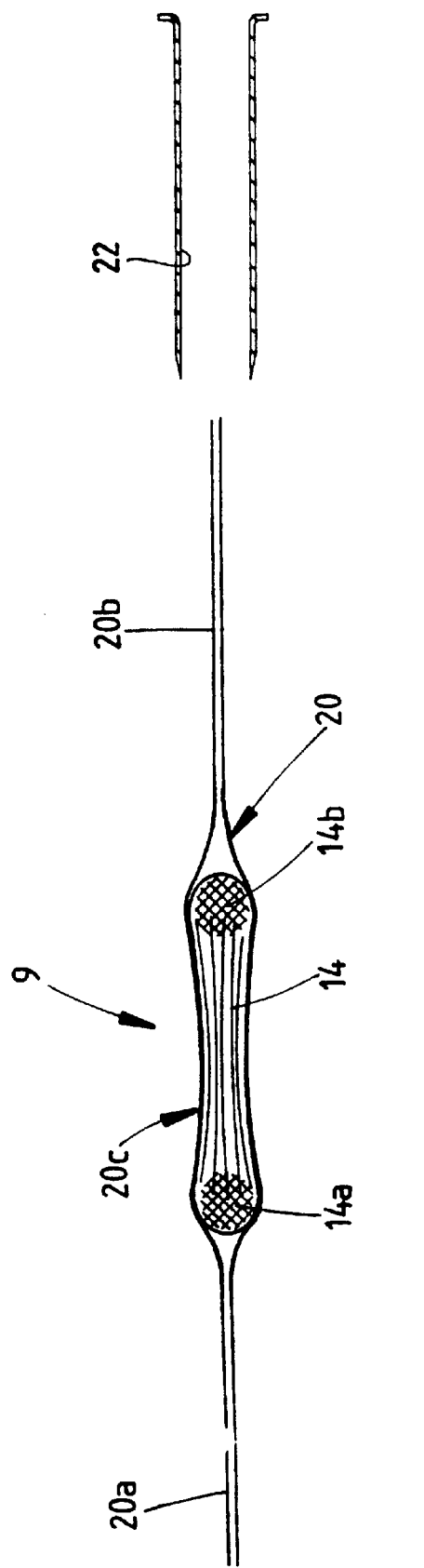
Figure 9:
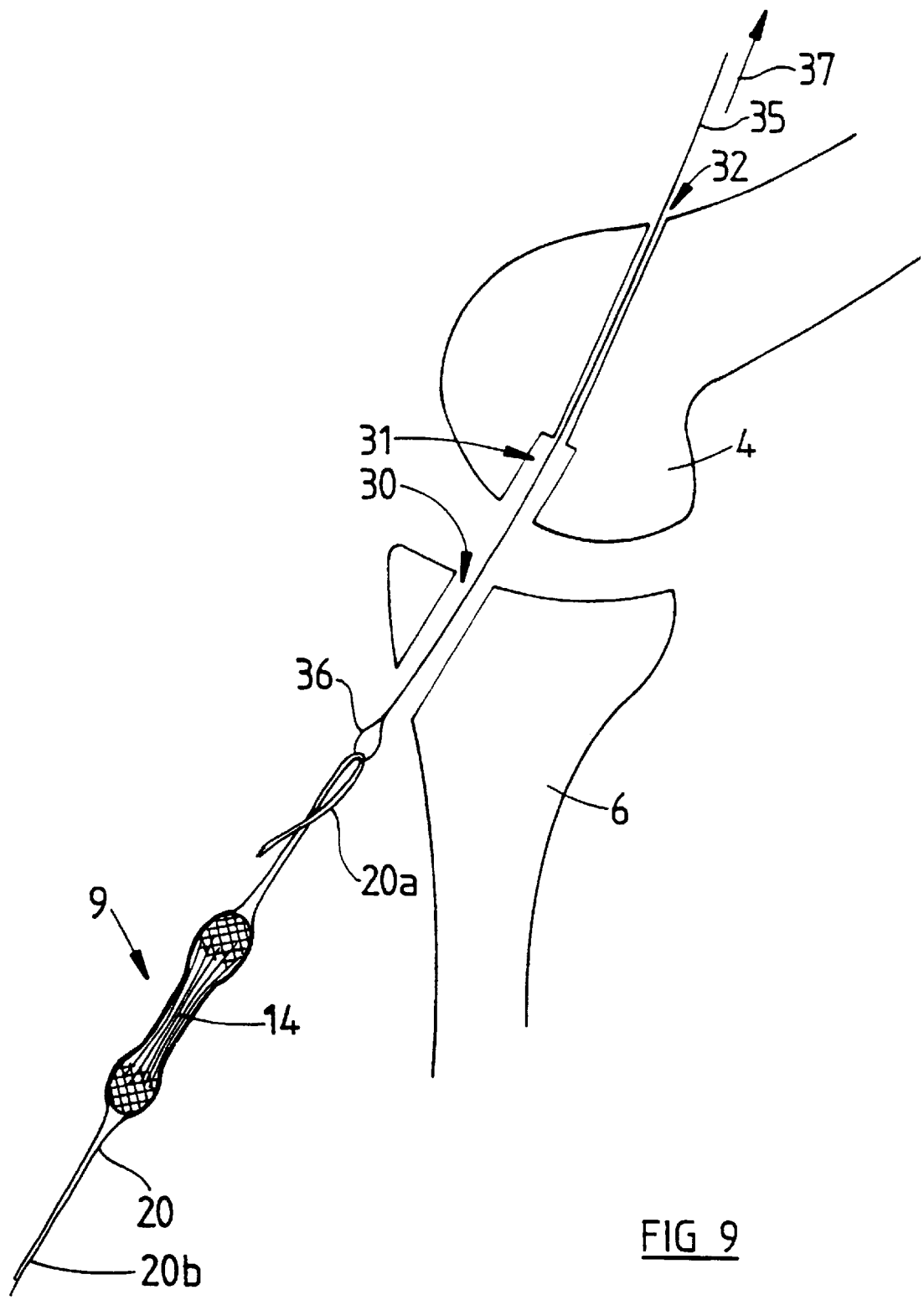
Figure 10:
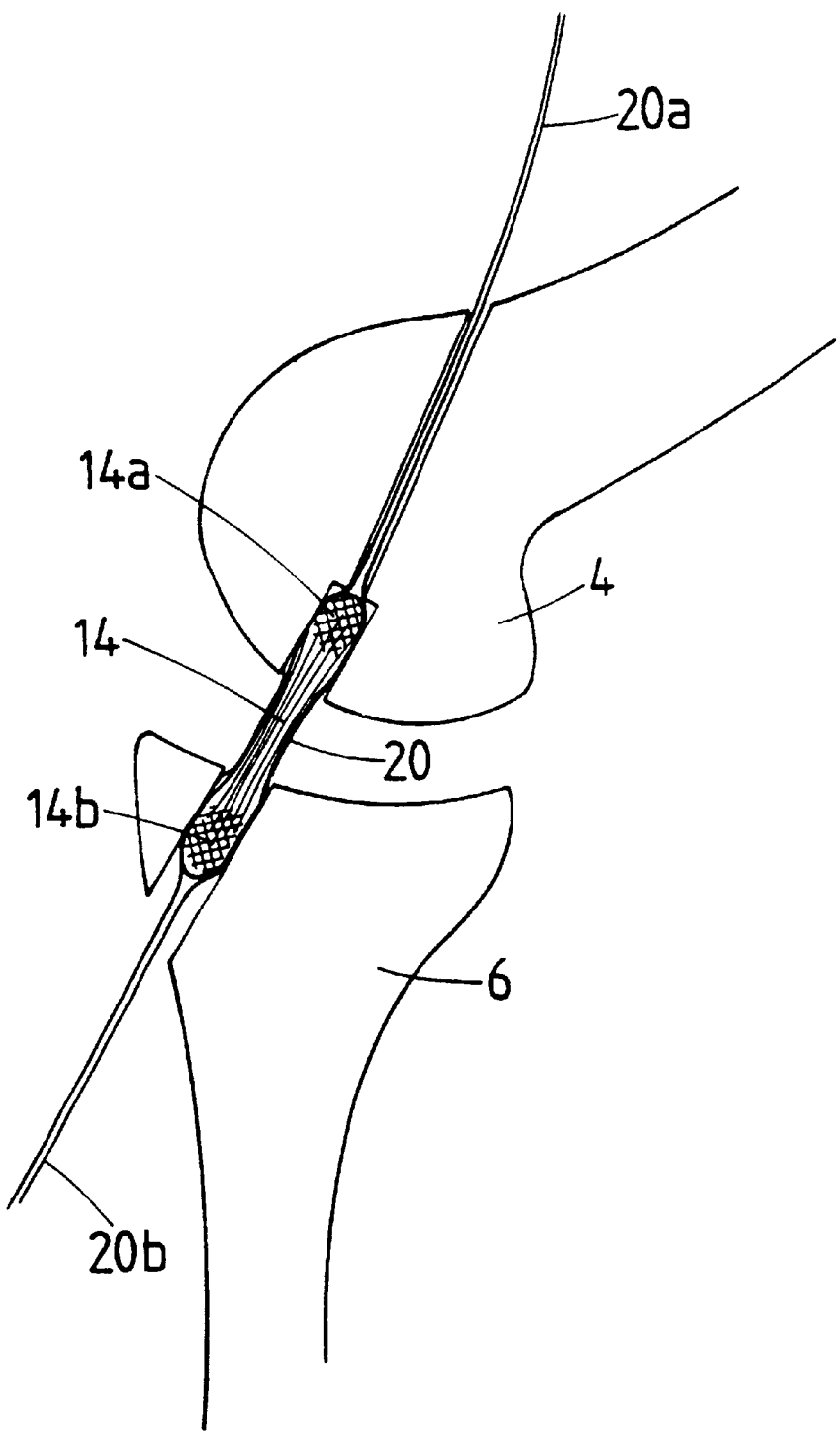
Figure 11:
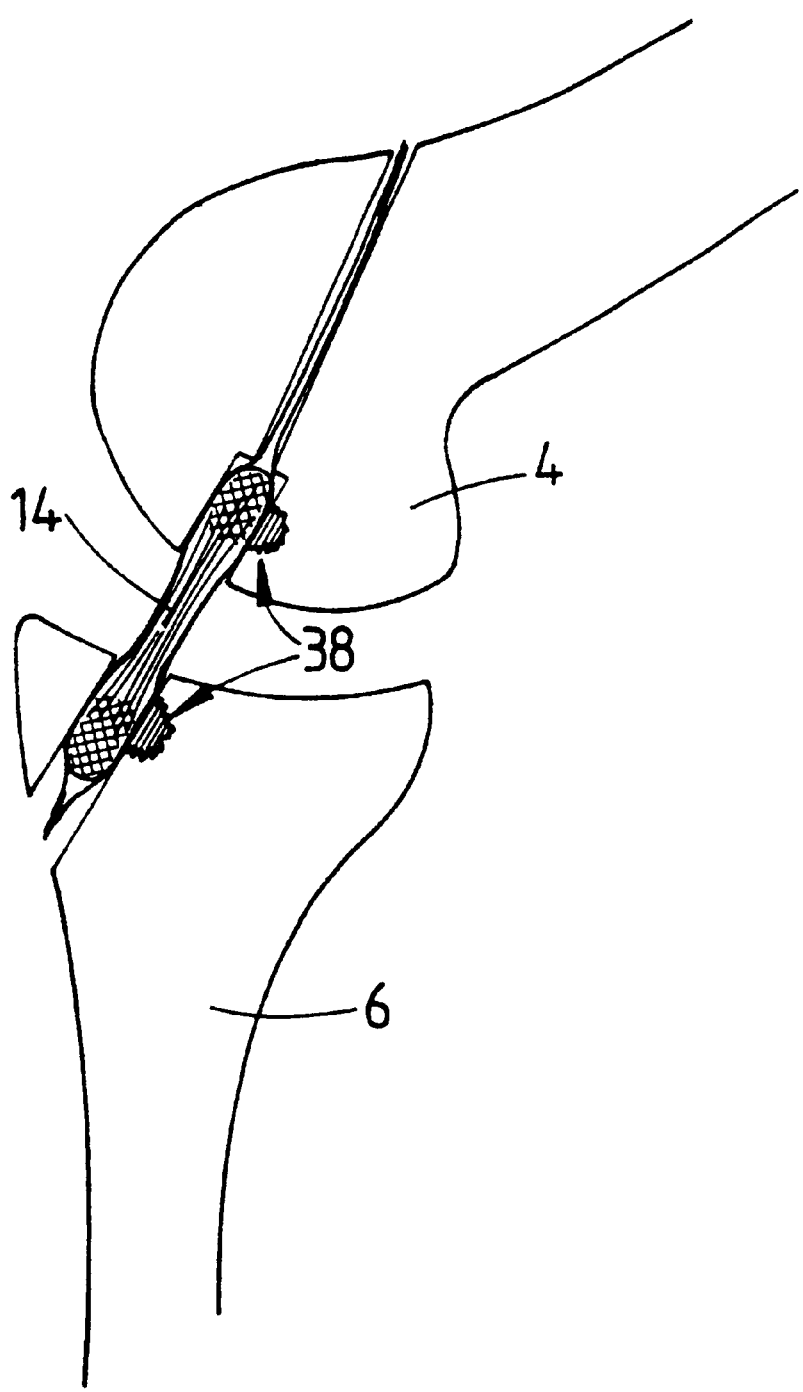

FIGS. 5 to 7 diagrammatically illustrate procedural steps for locating a graft in a sheath in accordance with the invention;

FIG. 8 diagrammatically illustrates a ligament graft assembly of the invention; and FIGS. 9, 10 and 11 are diagrammatic representations of a human knee joint shown from the side and illustrating the insertion of the graft therein with the use of the sheath, according to a preferred embodiment of the invention.

DETAILED DESCRIPTION

The principles of the invention will now be more fully described with reference to anterior cruciate ligament reconstructive surgery. It is to be understood, however, that this is by way of example only and the techniques of the invention are applicable in other forms of reconstructive surgery.

Anterior cruciate ligament reconstructive surgery is not an uncommon operation and is relatively successful, achieving acceptable results in the majority of patients undergoing the procedure. Most commonly, either the patella tendon or hamstring tendon are used as the basis for a graft of connective tissue, and each appear to have comparable results. However, a number of complications related to surgical technique can occur with both types of graft. The problems relate to the insertion of the graft, whether it be by open or arthroscopic methods, and the maintenance of the graft within the prepared drill holes.

With the increasing popularity of arthroscopic cruciate ligament reconstruction it has been a frequent observation that, when bone-patella tendon-bone grafts are used, difficulties can be encountered in the passage of the graft both through the tibial and femoral bone tunnels and through any soft tissue remnant within the knee. One of the problems concerns the adequate fixation of a suture to the bone-patella tendon-bone graft which will allow unrestricted force to be applied when attempting to engage the bone block in either of the tunnels.

Once the graft, be it bone-patella tendon-bone or hamstring tendon, is located within the bone tunnels problems of fixation remain. A number of devices including interference fit screws and the endo-button have been used, but there are now a number of examples where these forms of fixation have been shown to be inadequate.

A further additional problem which exists in relation to cruciate ligament reconstruction is accurate location of the isometric points of the anterior cruciate ligament and it has been conceived that embodiments of the present invention may have a role to play in improvement of this aspect of the surgery.

The preferred form of the present invention is a tubular mesh sheath of bio-absorbable thread designed to collapse and capture its contents. A specific purpose is to improve ligament and tissue grafting, such as in the reconstruction of the anterior cruciate ligament of the human knee. The sheath may be braided, woven or knitted, preferably from a plurality of strands of bioabsorbable material in such a way that axial tension applied to the sheath will cause the sheath to radially contract to ensheath a connective tissue graft, in use, therewithin. Furthermore, a component of the axial tension applied to the sheath is transmitted to the graft.

The strands from which the sheath is constructed is are at least partially bioabsorbable so that the sheath is at least substantially absorbed by the patients body in the recovery period following the reconstructive surgery. Suitable materials from which the bioabsorbable strands may be formed include polyglycolic acid, polylactic acid, poliglecaprone and polydioxanone, although other bioabsorbable materials may alternatively be employed. Suitable bioabsorbable materials and also suitable non-absorbable biocompatible materials which may be used in conjunction with the bioabsorbable strands will be apparent to those skilled in the art from the disclosures of U.S. Pat. Nos. 4,923,470 and 4,987,665, assigned to the American Cyanamid Company of Stamford, Conn. USA.

It is preferred that the sheath be formed from a plurality of strands in such a way that, if one strand breaks or is severed during use, the mesh structure of the remainder of the sheath is not adversely affected. This may be accomplished by the use of lock stitching or the like or by subjecting the sheath to heat in order to fuse the strands together where they are in contact with one another so as to thereby prevent running. In an alternative arrangement, an extruded tube of the material may be formed and slitted so as to form the expansible structure. The tubular sheath must be sufficiently radially expandable to allow a tissue graft to be inserted therein, and must be capable of contracting sufficiently to grasp the tissue graft therewithin when axial tension is applied. Preferably the sheath should be capable of expansion to a diameter significantly larger than that of the graft size, so that a tubular mesh holder can be inserted into an end of the sheath to facilitate insertion of the graft itself. It has been found that a sheath having a relaxed circumference of about 2 centimeters is appropriate for many applications.

Figure 1:
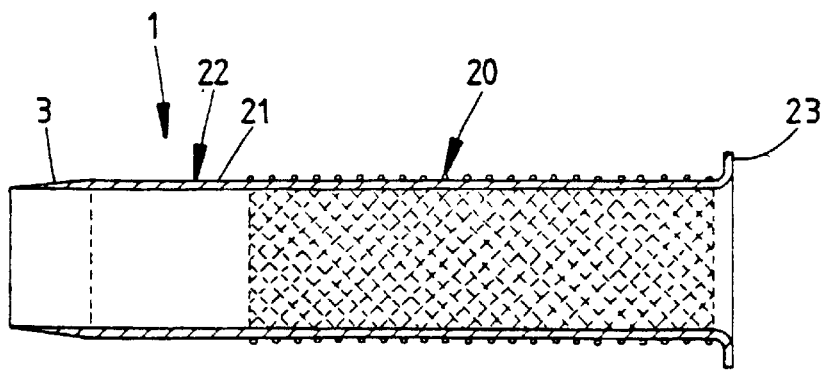
FIG. 1 is a cross-sectional view through a device for assisting in grafting in accordance with the invention.

FIG. 1 shows a surgical aid 1 constructed in accordance with the invention. The surgical aid comprises a tubular mesh holder 22 having a hollow cylindrical body 21 formed with a rounded flange 23 at one end. A sheath 20 is mounted on the mesh holder 22. In this condition the diameter of the sheath 20 is somewhat expanded so that it snugly fits on the body 21 and is prevented from falling off one end by means of the flange. The other end of the body 21 includes a chamfer 3 and the free end of the sheath 20 would normally be spaced axially relative to the chamfer 3. Preferably, the holder 22 is injection moulded from plastics material and has an inside diameter of about 9.5 mm and a wall thickness of about 0.5 mm. Its length including the chamfer 3 is preferably about 50 mm. The flange 23 preferably projects outwardly by about 2 mm.

As will be described in more detail below, the surgical aid 1 can be used in conjunction with a graft 14.

Figure 3:
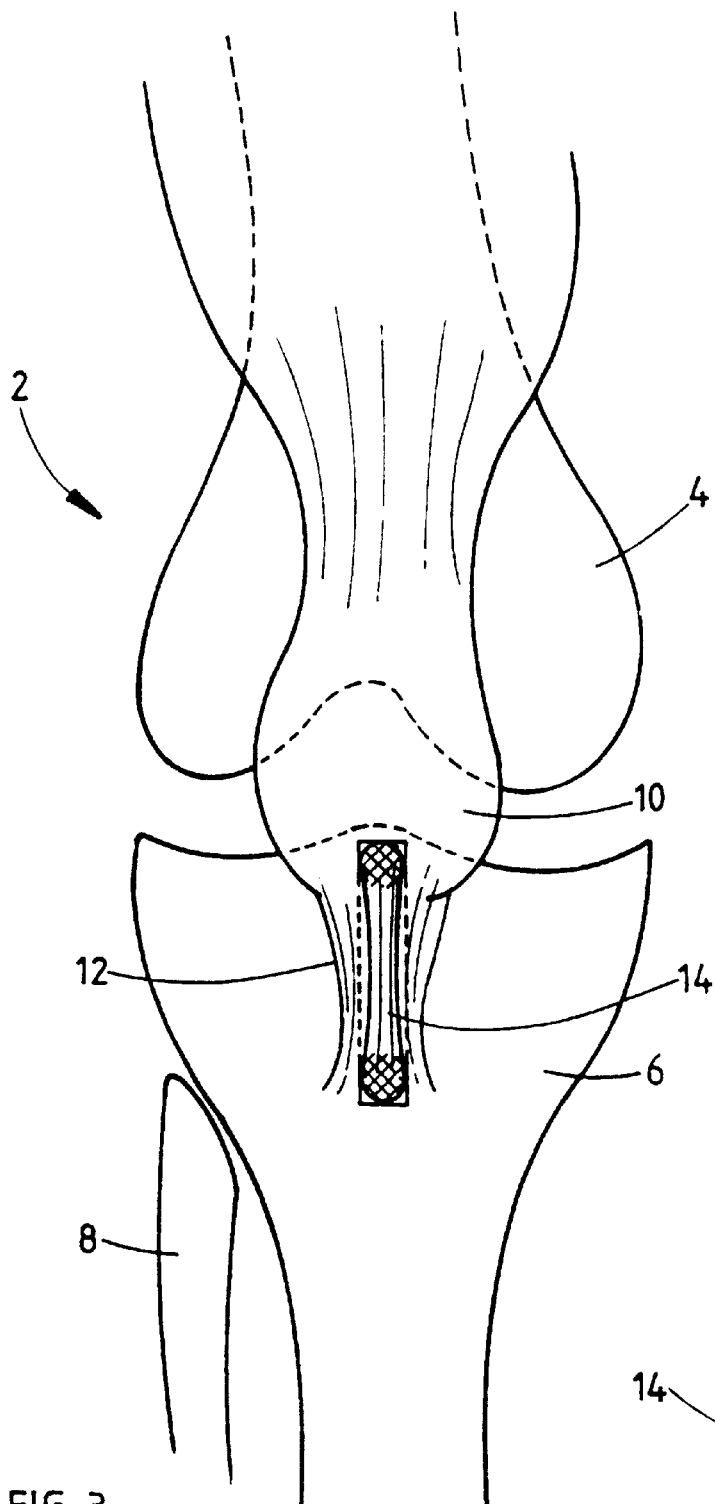
FIG. 3 is a schematic view of a human knee joint shown from the front illustrating removal of a portion of connective tissue.
Figure 4:
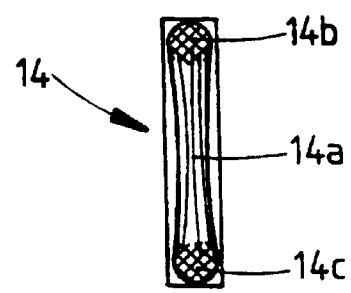
FIG. 4 illustrates a graft of connective tissue.

In FIG. 3 there is shown a diagrammatic representation of a human knee joint 2 shown from the front. The distal femoral process 4 and proximate processes of the tibia 6 and fibula 8 are shown, with the tibia coupled to the patella 10 by way of the patella ligament 12. A portion of the patella ligament 12 which is designated for removal to form the connective tissue graft is illustrated at 14, and shown removed and in greater detail in FIG. 4. The graft 14 comprises a portion of the patella ligament connective tissue 14a coupled at one end to a small block of patella bone 14b and at the other end to a small block of tibial bone 14c.

Having obtained the graft 14, the surgical aid 1 is employed to form a ligament graft assembly 9 as shown in FIG. 8. FIGS. 5 to 7 are schematic. As shown in FIG. 5, one end portion 20a is stretched from the chamfered end of the holder 22 so that about half the elongated length of the sheath 20 is removed. The graft 14 is then passed into the tubular mesh holder 22 from the flanged end 23 thereof until the end of the graft can be grasped at the other end of the mesh holder through the sheath portion 20a (FIG. 6). The graft is then held through the sheath material and drawn through the mesh holder 22 whilst the end of the sheath is pulled off the mesh holder (FIG. 7). Finally, the sheath is removed from the mesh holder 22 (FIG. 8) and to form the graft assembly 9 in which the graft 14 is ensheathed in an intermediate or central sheath 20c with extended end portions 20a and 20b of the sheath extending from the ends thereof. The length required of the tubular material of the sheath may depend upon the particular operation, but it is considered generally advantageous for additional length over the estimated required length to be provided since additional sheath material may be removed at the end of the procedure as described below. The extended length of the sheath 20 is preferably about 300 mm and the graft 14 is typically less than about 100 mm so that the end portions 20a and 20b are about 100 mm in length and function like strings or cords as will be described below.

FIG. 9 is a side cross-sectional diagrammatic representation of the human knee joint to be reconstructed. Receiving apertures 30 and 31 have been drilled in the tibia and femur processes 6 and 4, respectively, and having a nominal diameter of 10 mm. A narrower guide hole 32 extends from the aperture 31 to the superior surface of the femoral process 4. A guide wire 35 or the like extends through the guide hole 32 and receiving apertures 31 and 30 and out from the inferior surface of the tibial process 6 where it terminates at an eye 36 or other suitable attachment means. The end 20a of the graft assembly 9 is connected to the eye 36 of the guide wire by looping or tying the extended end portion 20a of the sheath material through the eye. The guide wire 35 is then pulled from the femoral end thereof in the direction generally indicated by arrow 37 so as to draw the ensheathed graft 14 through aperture 30. It may be desirable to maintain tension on the sheath 20 during this phase of the operation, by applying a suitable retarding force to the end portion 20b of the sheath. The surgeon can selectively pull the end portions 20a and 20b to correctly position the ends of the graft 14 in the apertures 30 and 31.

When the drawing of the graft into position is complete, the surgical site resembles the representation shown in FIG.

10. At this stage the graft is in situ with one end bone block fitted into femoral receiving aperture 31 and the other end bone block fitted into tibial receiving aperture 30. The guide wire may now be removed, and the end portions 20a and 20b of the sheath 20 extend from the femur and tibia through the respective guide hole 32 and receiving aperture 30 opening. The grafting operation is completed by removing the extending end portions 20a, 20b of the sheath at or near the surfaces of the bones 4 and 6.

The ends of the graft are now fixed within the receiving apertures. The graft fixation may be achieved in a number of ways, for example by coarse threaded interference fit screws 38, or the like, as are known in the art. Briefly, the screws are inserted in the apertures 31 and 32 so as to penetrate the gap (if any) between the bone blocks 14a and 14b and the apertures. The fixation means are applied through the material of the sheath so that the sheath is affixed in the joint along with the graft.

In some instances it may be advantageous for the graft to be affixed at its ends whilst under tension, and to achieve that tension may be applied by pulling on the ends 20a and 20b of the sheath while the graft is attached. This causes both the sheath and graft to be under tension.

Depending upon the material used to construct the sheath 20, the sheath will be at least substantially absorbed in a period of time following the surgical implantation thereof along with the graft. Whilst the sheath is in place it is able to relieve a portion of the strain which may be placed on the reconstructed tissue. However, not all of the strain is borne by the sheath to enable the graft to strengthen.

A number of advantages can be obtained through the utilisation of a sheath according the an embodiment of the present invention, as will be readily apparent to those skilled in the art from the foregoing and following description. Some of the advantageous effects include:

1. Enhancement of the delivery of a graft into its site of application because the graft 14 is enclosed within the sheath, it is less likely to be obstructed during passage through the mounting apertures.
2. Enhancement positioning of the ends of the graft in the mounting apertures by manipulation of the end portions 20a and 20b.
3. Enhancement of the fixation of the graft at each end.
4. Gradual transfer of load from sheath to graft due to bio-absorption of the sheath material.
5. Avoidance of load transfer and stress shielding that were characteristics of previous augmentation devices.
6. The ability to maintain the graft under tension during and after insertion.
7. Enhanced adherence of synovial tissue to graft and enhanced revascularisation and cellular proliferation within the graft.
8. The provision of a framework for the impregnation of growth enhancing factors, cultured cells or other pharmacological agents.
9. Because the sheath is formed from locked or run resistant material, it will still function even though some of the strands thereof may be damaged during the delivery and positioning steps. In addition, as the fibres which form the sheath 20 are gradually absorbed, the sheath will tend to maintain its integrity and thus avoid problems which might occur if portions of the sheath were to break away during the bioabsorption process.

It is also envisaged that various combinations of absorbable and non-absorbable material can be used to construct the mesh sheath of the present invention to alter to rate of degradation and permanent functional aspects of such grafts. For example, different types of poly-absorbable materials may alter the rate of absorption time of the mesh. Thus, where the surgeon, for example, believes that the tissue graft requires prosthetic support for a longer period of time, the sheath may be constructed to degrade more slowly and/or maintain a non-absorbable structural component.

Whilst this invention was originally designed for use in anterior cruciate ligament reconstruction using the patella tendon or hamstring tendon, a wide range of applications are envisaged for the mesh such as in reconstructing the posterior cruciate ligament, the Achilles tendon, the biceps tendons in the arm and shoulder or the tendons surrounding the wrist. Other uses may be readily apparent to those skilled in the art from reading this description of the invention.

Where a portion of hamstring tendon is to be used in knee construction surgery, it does not of course have the bone blocks at the ends. In this instance the part of the hamstring tendon which forms the graft is located within the sleeve in much the same way as described above. After placement of the ends of the graft in the receiving apertures, similar course threaded interference fit screws 38 are again used. In this application the material of the sheath is sandwiched between the graft and the screws and it has been found that significantly superior fixation occurs compared to known arrangements in which the operation is performed without the sleeve. It is thought that the increased improvement in fixation in this application would be more pronounced than in the case where blocks of bone are present at the ends of the graft.

Figure 2A:
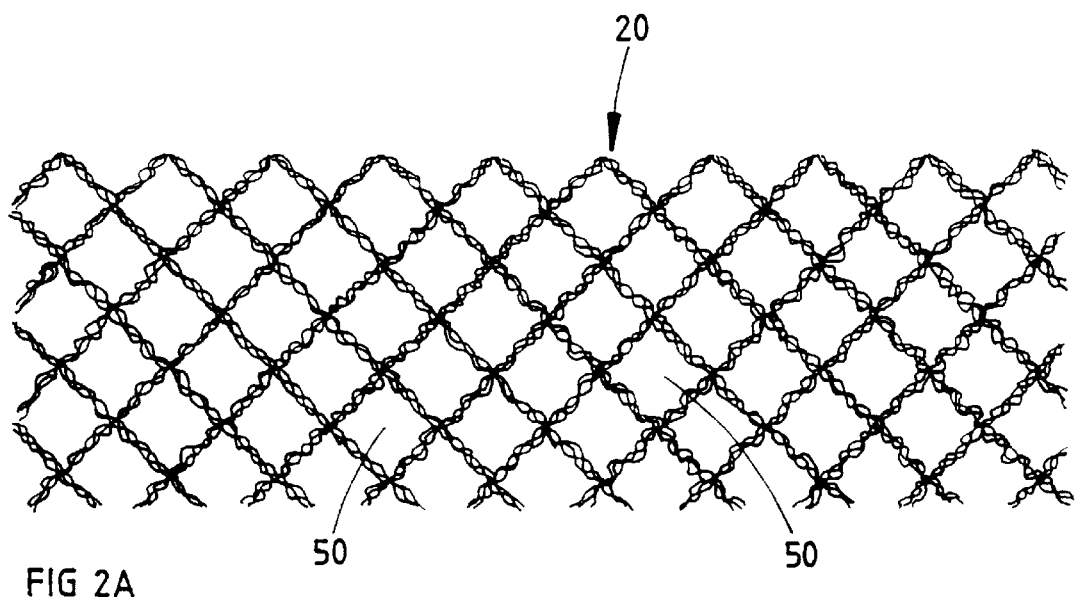
FIG. 2A is an enlarged schematic view of the mesh pattern of the sheath.
Figure 2B:
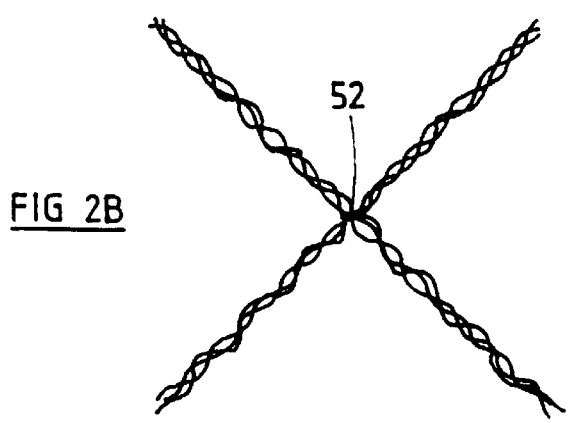
FIG. 2B is an enlarged schematic view of an intersection of the mesh pattern.

In a prototype construction the mesh sheath was formed by a commercial braiding process, although it is recognised that alternative manufacturing techniques may allow manufacture of a mesh of similar functionality. The mesh has been designed to maintain its integrity if failure of an individual strand occurs. In the prototype, a braiding machine normally used for making tachon lace was used because this is capable of braiding strands of the bioabsorbable material into an open mesh-like structure which is capable of substantial elongation. FIG. 2 schematically illustrates part of the mesh structure of the fabric of the tube 20. It will be seen that the mesh structure is relatively open having meshes 50 which are preferably square and having a mesh size in the range 2.5 to 3.5 mm, when the sheath 20 is laid flat in a non-expanded position. FIG. 2B schematically shows a knot-like structure 52 which is formed at the intersections between the meshes. The knot-like structure makes the fabric resistant to running or unravelling when some of the strands thereof are damaged or ruptured. In preparing the prototype sheath 20, twenty-four strands of bioabsorbable fibre were fed into the braiding machine. The fibre comprised 4/0 polyglycolic acid. The braiding machine produced a tubular sheath which when relaxed was about 1 cm in diameter on the flat. Expansion was achieved by placing a cylindrical object within the tube up to its maximum diameter, and contraction was observed when ends of the tube were placed under tension.

Preliminary work was done using an artificial anterior cruciate ligament made of rubber to demonstrate that by applying tension to each end of the tube that tension would develop within the synthetic graft. Grafts were then manufactured to be suitable for insertion in adult greyhound dogs.

Twelve dogs were chosen and anterior cruciate ligament reconstruction performed.

In dogs numbered one to three a routine anterior cruciate ligament reconstruction using a strip of illiotibial band was used. The strip of fascia remained attached distally at the level of the knee joint and was passed through the intercondylar region and over the lateral femoral condyle and then reattached distal to the joint line. This would be considered equivalent to an "over the top" technique with lateral reinforcement in a human patient.

In dogs numbered four to nine the same operation was performed but on these occasions the graft was contained within the poly-glycolic acid mesh.

In dogs numbered ten to twelve the same source of graft covered with mesh was used but on this occasion the graft was passed through a drill hole in the lateral femoral condyle and then reattached distally.

Dogs numbered one and two were sacrificed at six weeks, dog number three at twelve weeks, dogs numbered four to six at six weeks, dogs numbered seven to nine at twelve weeks and dogs numbered ten to twelve at twelve weeks.

Histological examination of the joint fluid, synovial lining and anterior cruciate ligament graft was performed in all cases.

The histological results were similar in all cases. There was no evidence of excessive fluid accumulation in the knee joints of those animals with mesh compared to those animals without mesh. There was no evidence of increased inflammatory response in those knees with mesh compared to those knees without mesh. There was no significant difference in the histological findings of the anterior cruciate ligament grafts with mesh or without mesh. There was no evidence of deleterious effect of the presence of mesh on graft or fibroblast formation within the graft.

The drill hole could be seen through the femoral condyle on post-operative X-ray but no evidence of an osteolytic reaction around the mesh was seen.

A second series of experiments was performed using beef femur. Graft from the patella tendon of beef was taken and fixed in the femoral condyle with the use of a fixation screw and subject to testing in a load testing machine. Comparisons were made between grafts inserted with and without the mesh.

The results in the load testing machine demonstrated a two fold increase in resistance to disassociation of the graft from the bone when using the mesh when compared to not using the mesh.

From this preliminary work it can be seen that the two fold aims of aiding the insertion and securing fixation using the mesh around an anterior cruciate ligament graft had been satisfied. Histological inspection demonstrated no deleterious effect of the presence of the mesh either on the joint itself or the graft.

The mesh sheath works on a similar principle to that of a Chinese finger trap to gain a secure and strong hold on the graft. This means that unrestricted tension can be placed on the graft when it is being passed through the joint there by ensuring that it seats correctly in the prepared drill holes and does not "hang up" on any protuberance either within or at the margins of the hole or from anything within the joint.

The tests have further demonstrated an additional benefit of the sheath to increase the security of fixation using interference fit screws. The results of load testing experiments of model cruciate graft implants for a comparison of mesh enhanced and non-mesh enhanced specimens are presented below.

Preparation

Twenty specimens of fresh bovine tendon were meticulously prepared by removal of peritenon and fat. The tendons were sized by trimming to 9.5 mm diameter using a tubular gauge.

Ten tendons were fixed into 100×50×38 mm blocks of particle board. Those blocks had been drilled with a 10 mm diameter hole to accept the tendon. Fixation was achieved using a Smith & Nephew Richards R. C. I. 8×25 mm interference screw which was inserted to finish flush with the lower surface of the block. The free end of the tendon was held in a clamp arranged so that there would be negligible slip during distraction.

Collapsable bioabsorbable mesh sheath was applied to ten tendons using the mesh carrier. This totally covered the tendon and provided a cord to allow easy introduction of the tendon into the wooden block and tendon clamp at each end. These specimens were fixed in the same fashion as the previous ten.

Testing

Testing was performed on a Unitomatic™ 20 load testing apparatus coupled to an Ametec P.C. and software. A 2 kilo-Newton load cell was selected. Distraction speed was set at 50 mm per minute in line with other similar testing sighted in the literature. A graphic representation of stroke (mm) v's force (Newtons) was produced and the maximum force generated was accepted as (Newtons) was produced and the maximum force generated was accepted as the failure load of the specimen. All data was recorded via a dot matrix printer.

Use of Particle Board

Particle board was chosen as the bone substitute because of its uniformity, strength and its textural similarity to cancellous bone. The load failure of these specimens were extremely close to those of the fresh bovine bone previously tested.

Mesh

The mesh used was braided from 20 ends of 4/0 "Vicryl" material manufactured by Johnson & Johnson.

Results

1. Tendon

I 706.3
II. 621.0
III. 594.3
IV. 608.5
V. 723.3
VI. 690.0
VII. 800.3
VIII 717.3
IX 755.0
X 970.5
Average 718.6

2. Tendon with mesh

I 969.0
II. 928.0
III. 925.5
IV. 973.5
V. 919.5
VI. 920.0
VII. 920.5
VIII 1166.5
IX 627.0 screw failed by pulling out of block
X 1190.0
Average 953.9

Observations

All specimens were carefully observed for method of failure. In all cases bar one, the specimen failed when the tendon was pulled free of the interference screw. This left the screw embedded in the block and a noticeable gouge in the side of the tendon where it had been withdrawn across the tynes of the screw. In one exception, a mesh covered graft actually pulled the screw from the block causing the specimen to fail at a lower load.

Close observation of failure of the mesh covered grafts showed that in all cases, except the above mentioned, rupturing of the mesh close to the point of fixation precipitated the failure of the specimen. This clearly indicated that the mesh was contributing substantially to the strength of the fixation.

Conclusion

The use of the mesh increased the load force required for failure of the graft fixation by an average of 235.3 kN or 32.7%. If the single case of screw failure was excluded this figure rises to 37.8%. The additional strength of fixation corresponded to the previously measure strength of the mesh in situ. It is clear from this work that improving the strength of the mesh would result in yet higher failure loads.

The foregoing detailed description has been presented by way of example only, and is not intended to be considered limiting to the invention which includes every novel feature and novel combination of features herein disclosed.

What is claimed is:

1. A sheath for use in ligament grafting comprising:
   a holder;
   a sheath including bioabsorbable fabric mesh material;
   said sheath having a first end and an intermediate portion in an axially relaxed state mounted on the holder for receiving a connective tissue graft in which the sheath has a first diameter in the range of from about 8 mm to about 15 mm; and
   said sheath having a second end in an axially tensioned and stretched state extending axially from the holder including a second diameter reduced from the first diameter, so that when the graft is pulled from the holder, the length of the sheath becomes at least five times its length in its relaxed state, whereby the connective tissue graft is captured in axial tension in the reduced sheath and a substantial length of the sheath extends axially from opposite ends of the graft.

2. A sheath as claimed in the claim 1 wherein the fabric mesh is formed from a number of interconnected strands.

3. A sheath as claimed in claim 2 wherein the mesh is of a size in the range of from about 2.5 mm to about 3.5 mm.

4. A sheath as claimed in claim 2 wherein the fabric mesh is formed such that it resists running or decomposing when one or more of the strands are ruptured.

5. A sheath as claim 4 wherein the strands which form the fabric mesh or partially fused in order to resist running or decomposing.

6. A sheath as claimed in claim 4 wherein the diameter of the strands is in the range of 0.06–0.55 mm.

7. A sheath as claimed in claim 4 wherein the strands comprise polyglycolic acid polymer.

8. A device for assisting in ligament grafting comprising:
   a holder having opposite ends and a hollow body which is open at the opposite ends for receiving a ligament graft;
   a sheath mounted over the hollow body;
   one of the opposite ends being flared to retain the sheath and the other of the opposite ends being tapered for removing the sheath;
   said sheath including bioabsorbable material;
   said sheath having an axially relaxed portion in an expanded diameter state in which the sheath seats adjacent the flared end of the hollow body; and
   said sheath being axially tensioned to a reduced diameter state extending axially from the tapered end of the holder in which the sheath has a length substantially greater than its length in the expanded diameter state, the arrangement being such that, in use, a ligament graft can be located within the hollow body, and axial tension applied to the sheath causes the ligament graft to be captured by the reduced diameter sheath to transfer the axial tension to the ligament and withdraw the ligament from the hollow body so that a substantial length of the sheath extends axially from opposite ends of the graft.

9. A device as amended in claim 8, wherein the hollow body has a length in the range from about 40 mm to about 75 mm.

10. A device as claimed in claim 8, wherein the sheath has a total length of from about 200 mm to about 350 mm with the sheath in its reduced diameter state.

11. A device as claimed in claim 10 wherein the total length is about 300 mm.

12. A method of facilitating placement of a ligament graft comprising:
   providing a holder having opposite ends and a hollow body which is open at the opposite ends for receiving a ligament graft;
   mounting an axially relaxed sheath over the hollow body;
   forming a ligament graft assembly by placing the ligament graft within the hollow body while the sheath is in an expanded diameter state on the hollow body;
   axially tensioning and elongating one end of the sheath and withdrawing the graft from the holder until the sheath and the graft are removed from the holder, so that the graft is captured in axial tension by an intermediate portion of the sheath, the one end of the sheath and an opposite end of the sheath being elongate and in a reduced diameter state so that a substantial length of each end of the sheath extends axially from opposite ends of the graft;
   forming a first opening in a first bone and a second opening in a second bone adjacent the first bone; and
   pulling one of said sheath ends through said openings so that the graft is carried with the sheath until a first end of the graft is located in the first opening and a second end of the graft is located in the second opening and the substantial length of the sheath extends from the first and second openings.

13. A method as claimed in claim 12 further comprising:
   passing a guide wire through said openings;
   connecting an end portion of the ligament graft assembly to the guide wire; and
   withdrawing the guide wire from said openings.

14. A method as claimed in claim 12 wherein the first opening is formed with a step so as to have a guide portion and a graft receiving portion.

15. A method as claimed in claim 12 further comprising:
   maintaining tension on said first and second ends of the sheath as said sheath is pulled into the openings.

16. A method as claimed in claim 12 further comprising:
   selectively pulling the first and second ends of the sheath in order to accurately place the graft in the first and second openings.

17. A method as claimed in claim 12 wherein one of the bones comprises a femur, the other bone comprises a tibia and the graft comprises part of a patella ligament having blocks of a patella bone at one end and the tibial bone at another end.

* * * * *